(12) United States Patent
Yamamoto

(10) Patent No.: US 9,295,592 B2
(45) Date of Patent: Mar. 29, 2016

(54) CUTTING APPARATUS

(75) Inventor: Hiroki Yamamoto, Kagawa (JP)

(73) Assignee: UNICHARM CORPORATION, Ehime-Ken (JP)

( * ) Notice: Subject to any disclaimer, the term of this patent is extended or adjusted under 35 U.S.C. 154(b) by 393 days.

(21) Appl. No.: 13/520,842

(22) PCT Filed: Jan. 7, 2011

(86) PCT No.: PCT/JP2011/050204
§ 371 (c)(1),
(2), (4) Date: Sep. 19, 2012

(87) PCT Pub. No.: WO2011/083857
PCT Pub. Date: Jul. 14, 2011

(65) Prior Publication Data
US 2013/0019733 A1    Jan. 24, 2013

(30) Foreign Application Priority Data
Jan. 9, 2010    (JP) .................................. 2010-003434

(51) Int. Cl.
*B65G 15/58*    (2006.01)
*A61F 13/15*    (2006.01)
(Continued)

(52) U.S. Cl.
CPC .......... *A61F 13/15723* (2013.01); *B26D 1/405* (2013.01); *B26D 7/018* (2013.01);
(Continued)

(58) Field of Classification Search
CPC ..................... Y10T 156/1734; Y10T 83/6476; A61F 13/15723; B26D 1/405; B26D 7/018; B65H 29/242; B65H 35/04; B65H 2301/33216; B65H 2301/44734; B65H 2301/42114; B65H 2406/323; B65H 2406/345; B65H 2801/57; B65G 15/58
USPC ............ 83/343–344, 346, 348, 351; 493/357, 493/427, 444, 440
See application file for complete search history.

(56) References Cited

U.S. PATENT DOCUMENTS

| 5,484,379 A * | 1/1996 | Stab .............................. 493/359 |
| 7,594,884 B2 * | 9/2009 | Robert ................... B65H 45/28 493/353 |

(Continued)

FOREIGN PATENT DOCUMENTS

| CN | 1917991 A | 2/2007 |
| EP | 1415628 A1 | 5/2004 |

(Continued)

OTHER PUBLICATIONS

Office Action dated Dec. 2, 2013, corresponds to Chinese patent application No. 201180005608.8.

(Continued)

*Primary Examiner* — Ned Landrum
*Assistant Examiner* — Nhat Chieu Do
(74) *Attorney, Agent, or Firm* — Hauptman Ham, LLP

(57) ABSTRACT

A cutting apparatus includes a holding conveying mechanism configured to convey a web using a holding surface, and a cutting mechanism configured to perform first cutting to cut the web conveyed while being held by the holding conveying mechanism along a crossing direction crossing a conveyance direction of the web and performing second cutting to cut the web along the crossing direction with a predetermined distance from the first cutting. The holding surface includes a main holding area configured to hold the web along the crossing direction between the first cutting and the second cutting, and an auxiliary holding area configured to hold the web by a holding power weaker than the holding power in the main holding area, at least in either upstream or downstream of the conveyance direction of the main holding area.

9 Claims, 5 Drawing Sheets

(51) Int. Cl.
*B26D 1/40* (2006.01)
*B26D 7/01* (2006.01)
*B65H 29/24* (2006.01)
*B65H 35/04* (2006.01)

(52) U.S. Cl.
CPC .......... *B65H 29/242* (2013.01); *B65H 29/243* (2013.01); *B65H 35/04* (2013.01); *B65G 15/58* (2013.01); *B65H 2301/33216* (2013.01); *B65H 2301/42114* (2013.01); *B65H 2301/44734* (2013.01); *B65H 2406/323* (2013.01); *B65H 2406/345* (2013.01); *B65H 2801/57* (2013.01); *Y10T 83/6476* (2015.04)

(56) References Cited

U.S. PATENT DOCUMENTS

| | | | | |
|---|---|---|---|---|
| 2003/0121614 | A1* | 7/2003 | Tabor et al. | 156/552 |
| 2007/0074953 | A1* | 4/2007 | McCabe | 198/377.08 |
| 2008/0196564 | A1* | 8/2008 | McCabe | 83/23 |
| 2008/0289468 | A1 | 11/2008 | Nakakado et al. | |

FOREIGN PATENT DOCUMENTS

| | | |
|---|---|---|
| JP | 9294769 A | 11/1997 |
| JP | 2005296 A | 1/2005 |
| JP | 2005000296 A | 1/2005 |
| JP | 2006230438 A | 9/2006 |
| JP | 2007260875 A | 10/2007 |
| JP | 2008237796 A | 10/2008 |
| JP | 2010142415 A | 7/2010 |
| JP | 2010240109 A | 10/2010 |
| WO | 2004/007329 A1 | 1/2004 |
| WO | 2005075163 A1 | 8/2005 |

OTHER PUBLICATIONS

Extended European Search Report issued on Aug. 27, 2014 in European Application No. 11731855.0.
International Search Report and Written Opinion for PCT/JP2011/050204, dated Apr. 12, 2011.

* cited by examiner

CUTTING APPARATUS

RELATED APPLICATIONS

The present application is National Phase of International Application Number PCT/JP2011/050204, filed Jan. 7, 2011, and claims priority from Japanese Application Number 2010-003434, filed Jan. 9, 2010.

TECHNICAL FIELD

The present invention relates to a cutting apparatus configured to cut an expanded web so formed that disposable worn articles including an elastic member are continued into each disposable worn article while conveying the web.

BACKGROUND ART

Conventionally, in a process of manufacturing disposable worn articles such as a disposable diaper, there is widely used a cutting apparatus configured to cut a web so formed that disposable worn articles are continued in its width direction into each disposable worn article while conveying the web (for example, Japanese Patent Application Publication No. 2006-230438 (Page 8, FIG. 1)).

In such a cutting apparatus, a rotation drum on which a plurality of absorbent pads corresponding to the dimension of the disposable worn article are arranged on the circumference is used. The web held by the absorbent pad is cut into units of disposable worn article by a blade arranged on a rotating cutter roller. Specifically, the blade arranged on the cutter roller abuts the web conveyed while being held onto the absorbent pad and cuts the web for each predetermined interval equivalent to the width of the disposable worn article.

Further, in the disposable worn article such as a disposable diaper, a gather is generally arranged by using a plurality of filament elastic members in order to increase the fitting provided between the disposable worn article and the wearer. Since the web conveyed by the rotation drum is held by the absorbent pad while being expanded to a certain degree, when one end of the width direction of the disposable worn article is cut by using the cutter roller, the gather is released and the released gather is contracted toward the other end of the width direction of the disposable worn article.

At a time point at which the one end of the width direction of the disposable worn article is cut, the other end of the width direction is not yet cut, and thus, the disposable worn article is deviated to the other end side of the width direction by the contraction of the gather. The result is that intervals at the center position of the product (disposable worn article) are not equal any more. That is, the intervals of the disposable worn article conveyed after being cut are not equal any more, and thus, it becomes not possible to stably convey toward a process of packaging the disposable worn article, which is performed after the cutting, and it is not possible to perform the exact packaging, either.

Moreover, the length on the one end side of the width direction of the disposable worn article becomes short, and thus, there arises a problem that the length on the one end side of the width direction and the length on the other end side of the width direction are not equal. In such a case, the appearance of the disposable worn article becomes asymmetric with respect to the width direction, and thus, the visual aesthetics of the product are damaged, and at the same time, shapes of the individual disposable worn articles are not equal, resulting in a problem that the form after the packaging is awkward.

SUMMARY OF THE INVENTION

Therefore, the present invention has an objective to provide a cutting apparatus capable of avoiding inconvenience of the irregular intervals at the center position of the disposable worn article during the conveyance, resulting from the fact that the lengths of the one end side and the other end side of the width direction of the disposable worn article are unequal, deterioration of the quality of appearance, and inconvenience encountered during the manufacture.

The feature of the present invention is summarized in that a cutting apparatus (cutting apparatus 1) configured to cut a web (web W) formed that elastic members are continuously disposed into units of disposable worn article (disposable diaper P) while conveying the web in an expanded state, including: a holding conveying mechanism (holding conveying mechanism 30) configured to convey the web using a holding surface (holding surface 32A), the holding conveying mechanism having the holding surface on which the web is held; and a cutting mechanism (cutting mechanism 20) configured to perform first cutting to cut the web conveyed while being held by the holding conveying mechanism along a crossing direction crossing a conveyance direction of the web and performing second cutting to cut the web along the crossing direction with a predetermined distance from the first cutting, wherein the holding surface includes: a main holding area (main holding area 301) configured to hold the web along the crossing direction between the first cutting and the second cutting, and an auxiliary holding area (auxiliary holding area 302) configured to hold the web by a holding power weaker than the holding power in the main holding area, at least in either upstream or downstream of the conveyance direction of the main holding area.

DESCRIPTION OF THE EMBODIMENTS

Subsequently, embodiments of a cutting apparatus according to the present invention will be explained with reference to the diagrams. In the following description of the diagrams, the identical or similar portions are assigned the identical or similar numerals. However, it should be noted that the diagrams are schematic and ratios of the respective dimensions do not justify the actual ones.

Therefore, the specific dimensions, etc., should be determined in consideration of the following explanations. Moreover, it is needless to say that relations and ratios among the respective dimensions differ among the diagrams. Further, in the following explanations, configurations having similar operation and effect are assigned the identical numerals, and the detailed explanations therefore are omitted.

(Embodiment)

Figure 1:
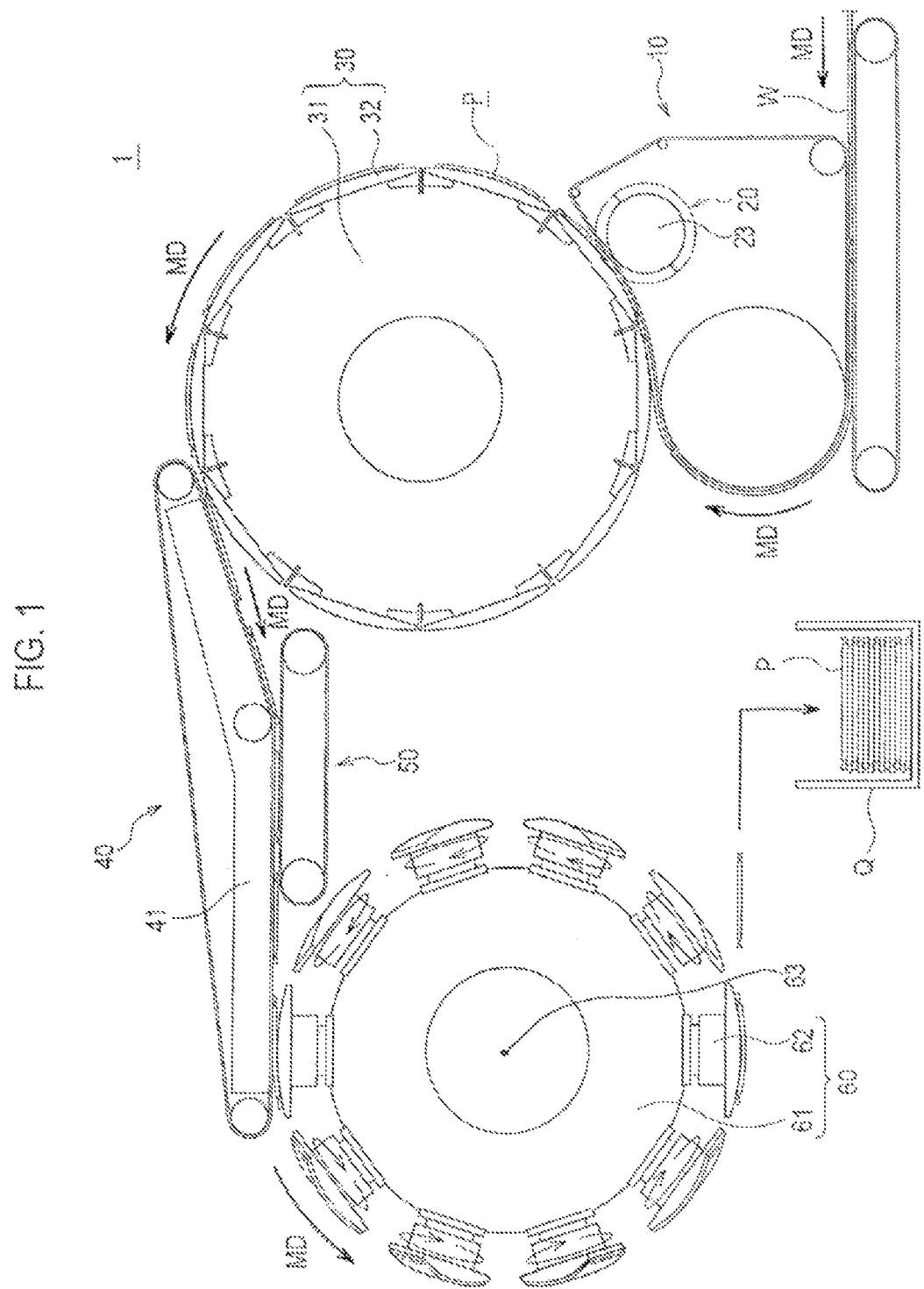
FIG. 1 is a side view in which a cutting apparatus 1 according to an embodiment of the present invention is seen from a direction perpendicular to a conveyance direction of a web W.

An overview of a cutting apparatus 1 according to an embodiment of the present invention will be explained. FIG. 1 is a side view in which the cutting apparatus 1 according to the embodiment of the present invention is seen from a direction perpendicular to a conveyance direction of a web.

As shown in FIG. 1, the cutting apparatus 1 includes: a conveying mechanism 10 configured to forward a continuous body (called "web W") to a conveyance direction MD that runs along a step of manufacturing a disposable worn article and to guide the web W to a cutting mechanism 20 and a holding conveying mechanism 30, which will be described later; the cutting mechanism 20 configured to cut the web W at a predetermined position; and the holding conveying mechanism 30 configured to hold the web W that is not yet cut for the conveyance to the conveyance direction MD along a conveyance path and convey an already-cut disposable diaper P to the conveyance direction MD. The cutting apparatus 1 further includes: a first hand-over mechanism 40 and a second hand-over mechanism 50 that hand over the disposable worn article that has been cut from the holding conveying mechanism 30 to a turnover device 60; and the turnover device 60 configured to change an orientation of the already-cut disposable worn article.

In this embodiment, the disposable worn article is the disposable diaper P including a waistband unit corresponding to a waistband of a wearer and a crotch unit corresponding to a crotch of the wearer (the detail will be described later with reference to FIG. 5).

Figure 2:
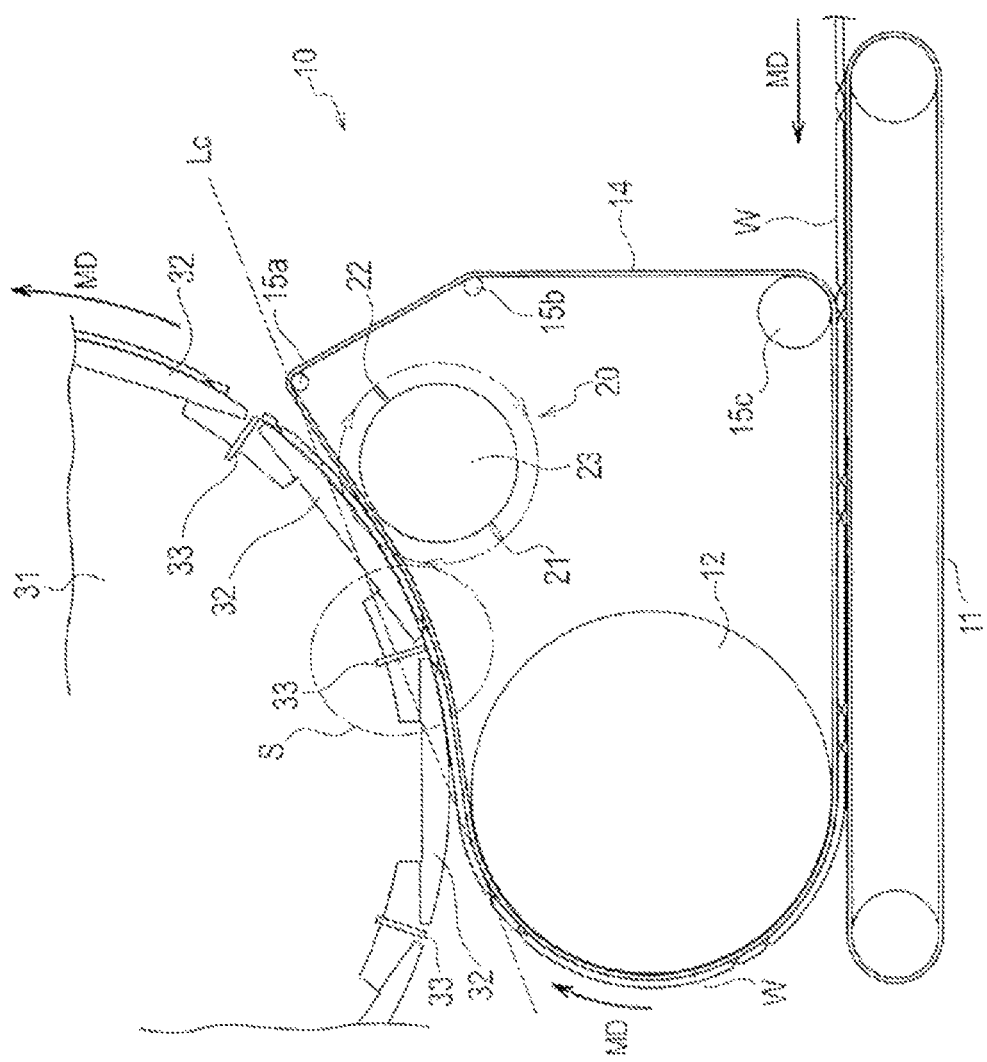
FIG. 2 is a side view in which one portion of a holding conveying mechanism 30, a cutting mechanism 20, and a conveying mechanism 10 in the cutting apparatus 1 according to the embodiment is seen from the direction perpendicular to the conveyance direction of the web W.

Subsequently, each configuration of the cutting apparatus 1 will be explained. FIG. 2 is a side view in which one portion of the conveying mechanism 10, the cutting mechanism 20, and the holding conveying mechanism 30 in the cutting apparatus according to the embodiment is seen from the direction perpendicular to the conveyance direction of the web W.

As shown in FIG. 2, the conveying mechanism 10 includes: a belt conveyor 11 on which the web W is conveyed; a large-diameter roller 12 configured to guide the conveyed web W to the cutting mechanism 20 and the holding conveying mechanism 30; and a press-down belt 14 configured to press down one portion of the web W onto the holding conveying mechanism 30. In this embodiment, the press-down belt 14 configures press-down means.

The press-down belt 14 is wound around: a large-diameter roller 23; and small-diameter rollers 15a, 15b, and 15c. The holding conveying mechanism 30, the large-diameter roller 23, and the small-diameter roller 15a are disposed so that a tangent line Lc common to an outer circumferential surface of the large-diameter roller 23 and an outer circumferential surface of the small-diameter roller 15a crosses an outer circumferential surface of the holding conveying mechanism 30.

Thus, in a section from the small-diameter roller 15c to the large-diameter roller 23, the press-down belt 14 conveys a non-continuous portion Wd (see FIG. 3) of the web W, which is sandwiched together with the belt conveyor 11, and in a section between the large-diameter roller 23 and the small-diameter roller 15a, the press-down belt 14 conveys one portion of the web W, which is sandwiched together with the outer circumferential surface (surface of a holding pad unit 32 described later) of the holding conveying mechanism 30. Specifically, when a downstream side of the conveyance direction MD of the web W is cut (first cutting described later), the press-down belt 14 holds the non-continuous portion Wd of the web W by the outer circumferential surface (main holding area 301 described later) of the holding conveying mechanism 30.

Subsequently, the cutting mechanism 20 will be explained. The cutting mechanism 20 is a rotary cutter, and so disposed that a rotation shaft (not shown) of the cutting mechanism 20 matches a direction perpendicular to the conveyance direction MD. At a predetermined position of the cutting mechanism 20, a cutter 21 and a cutter 22 are disposed along a direction crossing the conveyance direction MD.

The holding conveying mechanism 30 includes: a rotation drum 31 having a rotation shaft along the direction perpendicular to the conveyance direction MD; and a holding pad unit 32 arranged at an outer circumferential unit of the rotation drum 31. A plurality of holding pad units 32 are disposed at the outer circumferential unit of the rotation drum 31. Before and after cutting the web W, the holding pad unit 32 holds the web W (disposable diaper P in the case of after the cutting).

Among the plurality of holding pad units 32, anvils 33 are disposed. Each anvil 33 is a tooth-rest corresponding to the above-described cutters 21 and 22. The cutting mechanism 20 and the holding conveying mechanism 30 are disposed so that the cutters 21 and 22 disposed in the cutting mechanism 20 and the anvil 33 disposed in the holding conveying mechanism 30 abut each other in the case where there is no web W.

The cutting mechanism 20 performs the first cutting by the cutter 21 and the anvil 33 along the direction crossing the conveyance direction MD of the web W while conveying the web W that is being held between the holding conveying mechanism 30 and the press-down belt 14. After the first cutting, the cutting mechanism 20 and the holding conveying mechanism 30 rotate, and a second cutting is performed along the crossing direction by the cutter 22 and the anvil 33 with a predetermined distance from the first cutting. Herein, the predetermined distance includes a length along the conveyance direction MD of the holding pad unit 32. Also, the predetermined distance includes intervals of the anvils 33.

Subsequently, the holding conveying mechanism 30 will be explained. The holding conveying mechanism 30 includes: the rotation drum 31 and the holding pad unit 32 disposed at the outer circumferential unit of the rotation drum 31. The holding pad unit 32 is coupled to a suction pump not shown.

In this embodiment, the holding conveying mechanism 30 and the turnover device 60 are coupled by the first hand-over mechanism 40 and the second hand-over mechanism 50. The first hand-over mechanism 40 is a belt conveyor in which a through-hole is formed on the conveyance surface, and includes a suction box 41 including a suction mechanism configured to draw external air from the through-hole. As a result, the first hand-over mechanism 40 conveys the web W in a tightly adhering manner. The second hand-over mechanism 50 supports and conveys the web W in a section where the web W of the suction box 41 of the first hand-over mechanism 40 is not adhered.

Subsequently, the turnover device 60 will be explained. The turnover device 60 includes: a rotation pad support drum 61 having a rotation shaft 63 along the direction perpendicular to the conveyance direction MD; and a rotation pad unit 62 arranged at the outer circumferential unit of the rotation pad support drum 61. A plurality of rotation pad units 62 are disposed at the outer circumferential unit of the rotation pad support drum 61. The turnover device 60 is configured similarly to the holding conveying mechanism 30, and in addition, the turnover device 60 is so configured that the rotation pad unit 62 is able to rotate within an outer circumferential surface of the rotation pad support drum 61.

The rotation pad unit 62 rotates, while supporting the rotation pad unit 62, the holding surface by at least 90 degrees at the outer circumferential unit of the rotation pad support drum 61 so that the holding surface holding the disposable diaper P of the rotation pad unit 62 faces an outside in a radial direction of the rotation drum 61. That is, the turnover device 60 is capable of changing the orientation of the already-cut disposable diaper P toward the conveyance direction MD. For example, the turnover device 60 conveys every other one of a plurality of rotation pad units 62 by rotating 180 degrees.

Figure 3:
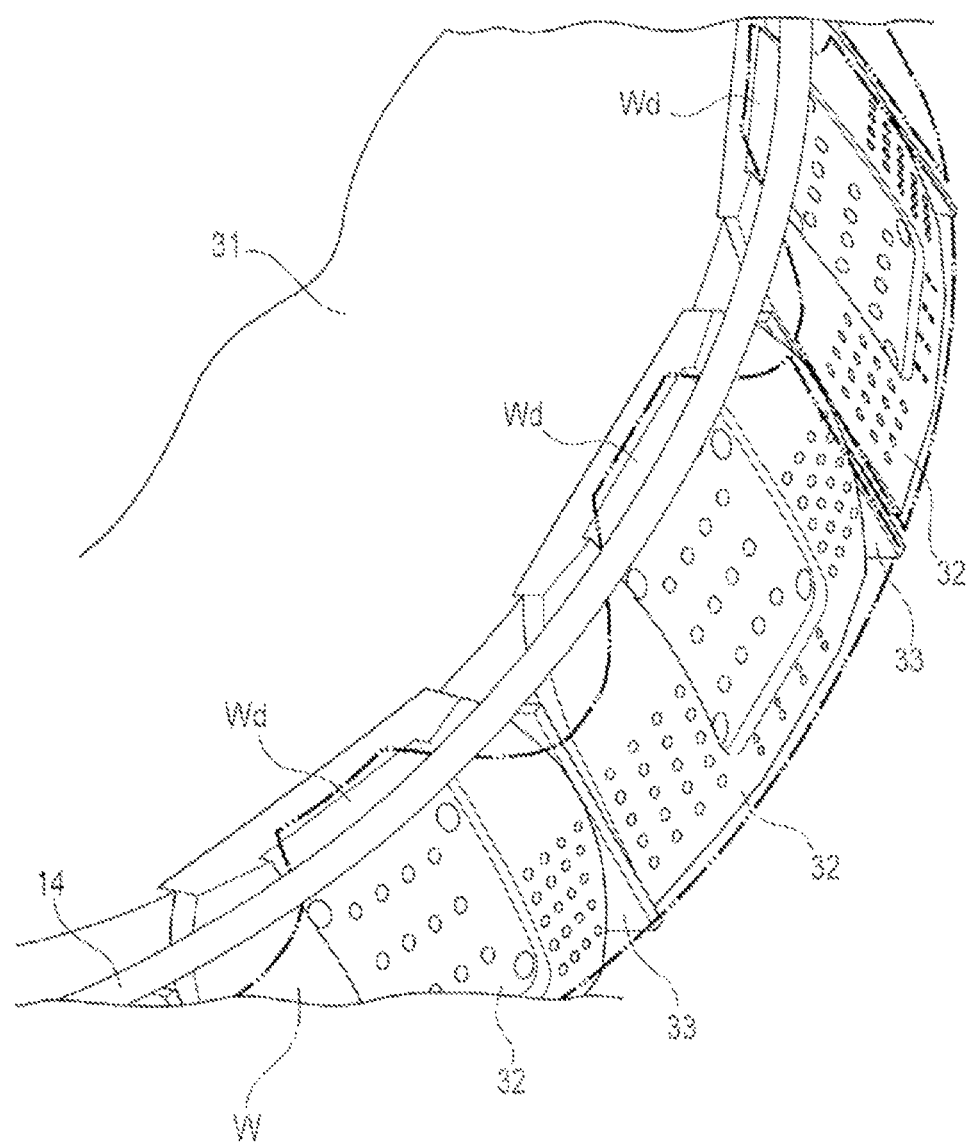
FIG. 3 is an enlarged perspective view of an area S shown in FIG. 2.
Figure 4:
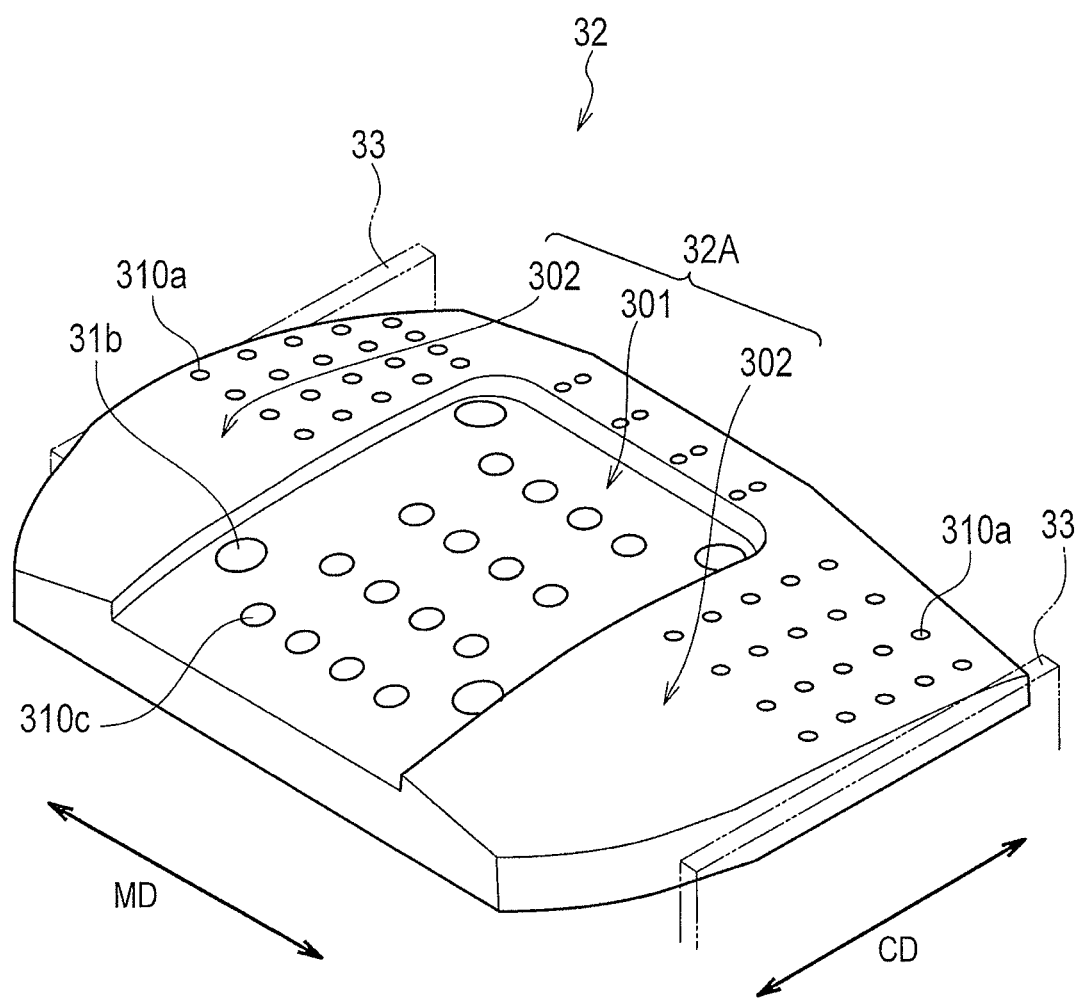
FIG. 4 is a perspective view explaining a holding pad unit.

Subsequently, the holding pad unit 32 will be specifically explained. FIG. 3 is an enlarged perspective view of an area S shown in FIG. 2. FIG. 4 is a perspective view explaining the holding pad unit 32. In FIG. 3, the web W in which the disposable diapers P are continued is indicated by an imaginary line. The web W is conveyed while being pressed down by the press-down belt 14 onto the holding pad unit 32 of the holding conveying mechanism 30. Moreover, the web W is pressed down by the press-down belt 14 onto the holding pad unit 32 of the holding conveying mechanism 30, and in this state, the web W is cut into each disposable diaper P by the cutting mechanism 20.

As shown in FIG. 4, the holding pad unit 32 includes a holding surface 32A on which intake holes 310a, 310b, and 310c are formed. The intake holes 310a, 310b, and 310c are communicated to a suction unit not shown. As a result, air is drawn from the intake holes 310a, 310b, and 310c. In this embodiment, the intake holes 310a, 310b, and 310c differ in hole diameter.

The holding surface 32A of the holding conveying mechanism includes a main holding area 301 and an auxiliary holding area 302. The main holding area 301 holds the web W along the perpendicular direction CD of the holding pad unit 32. Moreover, the auxiliary holding area 302 is positioned upstream or downstream in the conveyance direction MD of the main holding area 301.

In this embodiment, the auxiliary holding area 302 is set to possess a holding power (i.e., suction power) weaker than that of the main holding area 301. Specifically, the hole diameters of the intake holes 310b and 310c formed in the main holding area 301 are larger than that of the intake hole 310a formed in the auxiliary holding area 302.

Herein, the characteristic of the disposable diaper P will be explained. FIG. 5 is a schematic view explaining a state where a continuous body (web W) of the disposable diaper P is cut by the cutting apparatus 1 according to the embodiment.

In this embodiment, the disposable worn article is the disposable diaper P. The disposable diaper P (the same as the disposable diaper 100) includes a waistband unit 101 corresponding to the waistband of the wearer and a crotch unit 102 corresponding to the crotch of the wearer. At least in the crotch unit 102 of the disposable diaper P, an absorber 110 absorbing a bodily waste such as urine and feces is disposed. Moreover, in the waistband unit 101 of the disposable diaper P, a gather in which elastic members 111 are disposed continuously along the conveyance direction MD is formed.

The web W is so formed that the disposable diapers P (disposable diapers 100) are connected to one another in the waistband section 101. In the web W, between the adjacent crotch units 102, an air gap AR is formed. The air gap AR configures a leg hole 103 of the already-cut disposable diaper 100. The web W, which is conveyed in a state of being expanded in the conveyance direction MD, is cut into each disposable diaper P by the cutting mechanism 20.

In the holding conveying mechanism 30, the web W is disposed so that the already-cut disposable diaper P corresponds to the holding pad unit 32. To the main holding area 301, an area in which the absorber 110 of the web W corresponds. Moreover, to the auxiliary holding area 302, the waistband unit 101 of the web W corresponds.

In this embodiment, the surface of the holding pad unit 32 is processed to match a shape allowing for easily holding the disposable diaper in accordance with the structural characteristic of the above-described web W (disposable diaper P). That is, irregularities are formed on the holding surface 32A of the holding pad unit 32.

Figure 5:
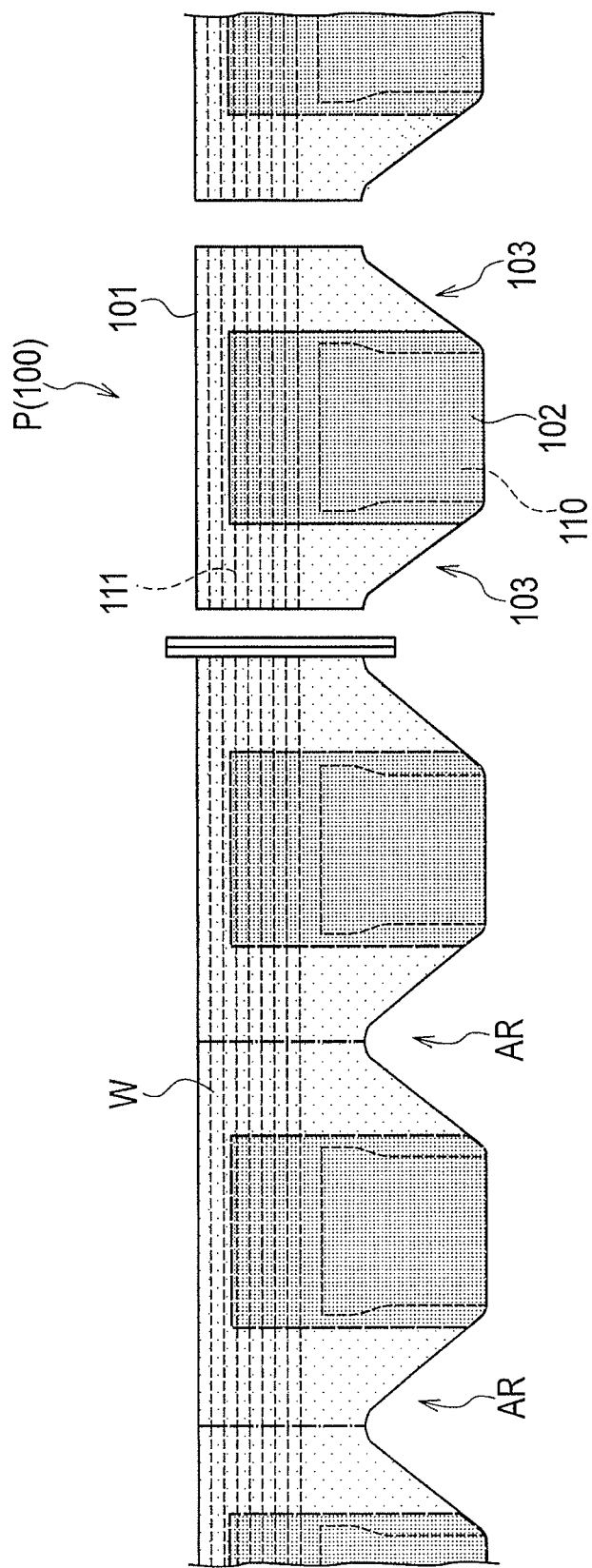
FIG. 5 is a schematic view explaining a state where a continuous body (web W) of a disposable diaper P is cut by the cutting apparatus 1 according to the embodiment.

As explained using FIG. 5, the absorber 110 is disposed in the crotch unit 102 of the disposable diaper P, and thus, the thickness of the crotch unit 102 is greater than that of the waistband unit 101. In this embodiment, the main holding area 301 is recessed, as compared to the auxiliary holding area 302, toward the center of the radial direction of the rotation drum 31.

In a first region of the web W contacting the main holding area 301, the absorber 110 is disposed, and thus, the permeability of the web W is lower than a second region of the web W contacting the auxiliary holding area 302. Therefore, as described above, the holding power (suction power) in the main holding area 301 is set to be stronger than that in the auxiliary holding area 302.

Moreover, the friction power of the auxiliary holding area 302 is greater than that of the main holding area 301. As one example, the surface of the main holding area 301 is so processed that the surface is roughened. Further, the surface of the auxiliary holding area 302 is so processed that the already-cut waistband unit 101 can easily slide, such as Teflon (registered trademark) process.

In either cross section of the conveyance direction MD and the perpendicular direction CD, the holding surface 32A of the holding pad unit 32 is formed in such a curved surface shape as to protrude toward the outside of the radial direction of the rotation drum 31.

As explained above, according to the embodiment-based cutting apparatus 1, on the holding surface (holding surface 32A of the holding pad unit 32) of the holding conveying mechanism 30 holding the web W, the main holding area 301 holding the web W and the auxiliary holding area 302 holding the web W by the holding power weaker than that of the main holding area 301 in either upstream or downstream of the conveyance direction MD of the main holding area 301 are provided. Thus, when the disposable diaper P is cut from the web W, the area equivalent to the disposable diaper P of the web W can be held by the main holding area 301 and the auxiliary holding area 302.

Thus, even when one end of the disposable diaper P is cut from the web W, it is possible to prevent the gather formed in the waistband unit 101 from contracting toward the other end of the width direction of the disposable diaper P.

Accordingly, it is possible to prevent deterioration of quality of appearance resulting from an unequal length of the one end side and the other end side of the width direction of the disposable diaper P and avoid inconvenience during the manufacture.

In the main holding area 301 and the auxiliary holding area 302, the through-hole (intake hole) communicated to the suction unit is formed, and thus, the web W (disposable diaper P) can be surely held in the main holding area 301 and the auxiliary holding area 302.

In one portion of the web W contacting the main holding area 301 of the disposable diaper P, the absorber 110 is disposed, and thus, the permeability of the web W is lower than that of the web W contacting the auxiliary holding area 302. In this embodiment, the holding power (suction power) in the main holding area 301 corresponding to a portion where the permeability of the web W (disposable diaper P) is low is set to be stronger than the holding power in the auxiliary holding area 302. As a result, at the center portion of the holding pad unit 32, the web W (disposable diaper P) can be surely held.

Before the cutting mechanism 20, one portion of the web W is sandwiched by the holding conveying mechanism 30 and the press-down belt 14, and thus, when the disposable diaper P is cut from the web W, it is possible to surely hold the web W (disposable diaper P), making it possible to prevent the finished shape of the already-cut disposable diaper P from becoming unequal.

The holding power (suction power) in the auxiliary holding area 302 is set to be lower than that of the main holding area 301. Moreover, the friction power of the auxiliary holding area 302 is processed to be greater than the friction power of the main holding area 301.

This allows the waistband unit 101 of the disposable diaper P in which the elastic member 111 is disposed to gradually return to the side of the center portion of the disposable diaper P (i.e., the crotch unit 102 in which the absorber 110 is disposed) after the waistband unit 101 is cut from the web W.

Therefore, it is possible to prevent an unnecessary stress from being applied to the waistband unit 101 of the already-cut disposable diaper P, making it possible to prevent the finished shape of the already-cut disposable diaper P from becoming an unnatural form.

The holding surface 32A of the holding pad unit 32 is processed to match a shape allowing for easily holding the disposable diaper P in accordance with the structural characteristic of the above-described web W (disposable diaper P). That is, the main holding area 301 is recessed, as compared to the auxiliary holding area 302, toward the center of the radial direction of the rotation drum 31. Thus, the area where the absorber 110 of the disposable diaper P is disposed in fitted into the recess, and thus, deviation of the conveyance direction MD or the perpendicular direction CD can not easily occur when the web W (disposable diaper P) is disposed on the holding surface 32A of the holding pad unit 32. Accordingly, when the disposable diaper P is cut from the web W, the web W (disposable diaper P) can be surely held.

In this embodiment, for example, the turnover device 60 conveys every other one of a plurality of rotation pad units 62 by rotating by 180 degrees. In this way, the disposable diaper P housed in a wrapping package Q can be oriented in a nested manner. The thickness of the disposable diaper P differs in the waistband unit 101 and the crotch unit 102, and thus, when the disposable diaper P housed in the wrapping package Q is orientated in a nested manner, the height of the wrapping package Q can be suppressed, making it possible to make the visual quality of the packaged form beautiful.

(Another Embodiment)

As described above, the content of the present invention has been disclosed through the embodiments of the present invention; it should not be understood that the description and the diagrams, one portion of the disclosure, restrict the present invention. From this disclosure, a variety of alternate embodiments, embodiments, and applicable techniques will become apparent to one skilled in the art.

For example, the embodiment of the present invention can be modified as follows: In the above-described embodiment, the explanation has been given of the configuration that the web W held onto the holding conveying mechanism 30 is cut, the disposable diaper P formed as a result of the cutting is conveyed to the turnover device 60 by the first hand-over mechanism 40 and the second hand-over mechanism 50.

In this embodiment, when the downstream side of the conveyance direction MD of the web W is cut (first cutting described later), the press-down belt 14 is used as means configured to press down the one portion of the web W (non-continuous portion Wd) toward the outer circumferential surface (main holding area 301 described later) of the holding conveying mechanism 30. However, the present invention is not limited to the configuration shown in FIG. 2. Other means except for a belt can be used.

The rotation angle in the turnover device 60 is not limited to 180 degrees. The angle may be appropriately changed according to the orientation of the disposable diaper P at the time of enclosure into the wrapping package Q. For example, the rotation angles of the rotation pad unit 62 may be set to 90 degrees and 270 degrees alternately. The turnover device 60 may not always be arranged.

Moreover, the first hand-over mechanism 40 and the second hand-over mechanism 50 may not always be arranged. For example, the turnover device 60 may be disposed at the position where the holding conveying mechanism 30 is disposed. In this way, while the disposable diaper P is conveyed, the already-cut disposable diaper P can change its orientation with respect to the conveyance direction Md.

In this embodiment, the hole diameters of the intake holes 310b and 310c formed in the main holding area 301 are larger than that of the intake hole 310a formed in the auxiliary holding area 302.

However, when the air gap 71 is imparted with a partition so that the through-hole formed in the main holding area 301 and that formed in the auxiliary holding area 302 are communicated to suction pumps different in suctioning power, the holding power (suctioning power) in the main holding area 301 can be made stronger than that in the auxiliary holding area 302.

Thus, needless to say, the present invention includes a variety of embodiments not described here. Therefore, the technical scope of the present invention is only defined by the invention specific matters according to the claims reasonably derived from the above description.

The entire contents of Japanese Patent Application No. 2010-003434 (filed on Jan. 9, 2010) are incorporated in the present specification by reference.

INDUSTRIAL APPLICABILITY

According to the characteristic provided by the present invention, it is possible to provide a cutting apparatus capable of avoiding inconvenience of the irregular intervals at the center position of the disposable worn article during the conveyance, resulting from the fact that the lengths of the one end side and the other end side of the width direction of the disposable worn article are unequal, deterioration of the quality of appearance, and inconvenience encountered during the manufacture.

The invention claimed is:

1. A cutting apparatus configured to cut a web in which elastic members are continuously disposed into disposable articles while conveying the web in an expanded state, said cutting apparatus comprising:
    a holding conveying mechanism configured to convey the web along a conveyance path using a holding surface, the holding conveying mechanism having the holding surface on which the web is held;
    a cutting mechanism configured to perform
        first cutting to cut the web conveyed while being held by the holding conveying mechanism along a crossing direction crossing a conveyance direction of the conveyance path of the web, and
        second cutting to cut the web along the crossing direction a predetermined distance from the first cutting; and a press-down member configured to press down a portion of the web onto the holding surface at least during the first cutting, wherein the holding surface includes:

a main holding area configured to hold the web, by a first holding power, along the crossing direction between the first cutting and the second cutting, and an auxiliary holding area configured to hold the web, by a second holding power weaker than the first holding power in the main holding area, at least in either upstream or downstream of the main holding area in the conveyance direction, the main holding area is recessed as compared to the auxiliary holding area, the cutting mechanism includes a cutter positioned at a first side of the conveyance path, the holding conveying mechanism is positioned at a second side of the conveyance path, the second side being opposite to the first side, the holding conveying mechanism further comprises an anvil configured to cooperate with the cutter of the cutting mechanism, the press-down member is sandwiched between the holding conveying mechanism and the cutting mechanism in a direction perpendicular to both the crossing direction and the conveyance direction, and the press-down member is disposed adjacent to the anvil in the crossing direction, without overlapping the anvil in the direction perpendicular to both the crossing direction and the conveyance direction.

2. The cutting apparatus according to claim 1, wherein the holding conveying mechanism includes:

a holding pad unit including the holding surface on which an intake hole to suction air is formed.

3. The cutting apparatus according to claim 2, wherein the main holding area is configured to contact a first region of the web, the auxiliary holding area is configured to contact a second region of the web, and said first region of the web has a permeability smaller than a permeability of said second region of the web.

4. The cutting apparatus according to claim 2, wherein the holding pad unit includes the recess, the main holding area defines a bottom surface of the recess, and the auxiliary holding area is flush with an upper surface of the recess.

5. The cutting apparatus according to claim 4, wherein each of the disposable articles includes an absorber for absorbing liquid, and the recess is formed to receive the absorber of one of the disposable articles.

6. The cutting apparatus according to claim 1, further comprising a turnover device configured to change a direction of disposable articles cut from the web by the cutting mechanism, wherein the turnover device includes a rotation pad support drum having a rotation shaft, a plurality of rotation pad units are arranged for each predetermined interval at an outer circumferential unit of the rotation pad support drum, each of the rotation pad units having a holding surface for holding one of the disposable articles, and the rotation pad support drum is configured to rotate the holding surfaces of the rotation pad units by at least 90 degrees in a state where the rotation pad units are held so that the holding surfaces of the rotation pad units face an outside of the rotation pad support drum in a radial direction.

7. The cutting apparatus according to claim 1, wherein the web includes:

a waistband unit corresponding to waistbands of the disposable articles; and a plurality of crotch units of the disposable articles, on the web, an air gap is arranged between the adjacent crotch units, and the cutting apparatus is configured to cut the web corresponding to the respective air gaps.

8. The cutting apparatus according to claim 1, further comprising a conveying mechanism including:

a large diameter roller;

a small diameter roller; and the press-down member being a belt configured to move around the large diameter roller and the small diameter roller.

9. The cutting apparatus according to claim 8, wherein a tangent line common to an outer circumferential surface of the large-diameter roller and an outer circumferential surface of the small-diameter roller crosses the holding surface of the holding conveying mechanism.

* * * * *